United States Patent [19]

Reifsnider et al.

[11] Patent Number: 5,305,645
[45] Date of Patent: Apr. 26, 1994

[54] DYNAMIC MEASUREMENT OF MATERIAL STRENGTH AND LIFE UNDER CYCLIC LOADING

[75] Inventors: Kenneth L. Reifsnider; Ahmad Razvan; Mehran Elahi, all of Blacksburg, Va.

[73] Assignee: The Center for Innovative Technology, Herndon, Va.

[21] Appl. No.: 878,718

[22] Filed: May 4, 1992

[51] Int. Cl.[5] .............................................. G01N 3/32
[52] U.S. Cl. ..................................................... 73/808
[58] Field of Search ................... 73/808, 811, 810, 813

[56] References Cited

U.S. PATENT DOCUMENTS

| | | |
|---|---|---|
| 3,007,335 | 11/1961 | Huyser et al. |
| 3,187,565 | 6/1965 | Kreiskorte et al. ............... 73/811 X |
| 3,563,086 | 2/1971 | Reed, Jr. |
| 3,589,175 | 6/1971 | Bock |
| 3,664,179 | 5/1972 | Danko et al. ..................... 73/808 X |
| 3,933,032 | 1/1976 | Tschoegl .......................... 73/813 X |
| 3,969,930 | 7/1976 | Prevorsek et al. ................ 73/811 X |
| 4,064,745 | 12/1977 | Gaddum ........................... 73/808 X |

*Primary Examiner*—Jerry W. Myracle
*Attorney, Agent, or Firm*—Whitham & Marhoefer

[57] ABSTRACT

A conventional dynamic testing machine, such as an MTS (Material Test System) is modified to allow for a new method for dynamically monitoring fatigue damage in a specimen. Load and stroke signals are used to determine phase angle and gain frequency response parameters for a specimen as it is cyclically loaded. Although the cycles required for specimens to fatigue to failure varies greatly from specimen to specimen, the phase shift between the load and stroke signals as well as the gain of the stroke signal remains fairly constant from specimen to specimen. These characteristic parameters can be used to accurately determine the percent of life remaining and residual strength in other specimens.

13 Claims, 8 Drawing Sheets

DYNAMIC MEASUREMENT OF MATERIAL STRENGTH AND LIFE UNDER CYCLIC LOADING

BACKGROUND OF THE INVENTION

1. Field of the Invention

The present invention generally relates to a method for accurately determining the percentage of life remaining in a polymeric or composite material which is undergoing cyclic loading. More particularly, the invention is related to determining rate of damage and total damage of a material by measuring the frequency response of the material.

2. Description of the Prior Art

Polymeric and composite materials are becoming more widely used in engineering applications that have traditionally employed metals. For example, aircraft wings, gears and cams, automobile body parts, space vehicle parts, as well as many other applications now employ polymeric and composite materials. It is generally not possible to reproduce in a laboratory all of the engineering environments in which such components must serve. It is particularly difficult to establish the nature of long-term parameters from laboratory tests that cannot be conducted over the required service life of the component.

Many engineering applications involve applied loads that vary in time. The behavior of materials under these conditions is generally characterized by applying cyclic loading in a "fatigue" test. Various cyclic tensile and compressive amplitudes are generally applied, and the number of cycles required to fail the material under those conditions is recorded. Fatigue damage is evidenced by a decrease in strength and stiffness. In some cases, tests may be terminated after some period of cyclic loading and residual strength determined by breaking the specimen material. The data from such destructive tests are usually characterized by empirical means and generalized by implication or extrapolation to a variety of service conditions for which the materials were not specifically tested in the laboratory.

Additionally, the number of cycles required to fail a material varies widely even among similar samples of like material composition. One specimen may fail after only 100 cycles, while another may last for 1,000,000 cycles. Many specimens are tested to determine a median life; however, for any given sample, this could be a very inaccurate predictor of life.

The static nature of prior art fatigue tests is not desirable since every time the test is stopped, the initial conditions of the forced vibrations are altered. Therefore, in order to fully understand the fatigue behavior of the materials as a function of stiffness change, it is desirable to monitor the dynamic response of the specimen continuously over time.

One prior art method for dynamically monitoring the fatigue of a composite specimen has involved the use of a strain gauge. In this method, a strain gauge is secured to the surface of a sample and the sample is cyclically loaded with the output of the strain gauge being indicative of the stiffness change for the sample. It is assumed that the fatigue measured at the point of attachment for the strain gauge is the same for the rest of the sample. Therefore, as the strain gauge is cyclically loaded, it begins to stretch further and further and this increased stretching is reflected by a change in the electrical output of the strain gauge.

Another prior art method for dynamically monitoring fatigue has involved the use of extensometers. In this method, an extensometer is adhesively attached over a surface area of the sample. As the sample is cyclically loaded, the extensometer outputs electrical signals related to the changes in the surface area of the sample adjacent to the extensometer. Just as in the case of the strain gage, discussed above, it is assumed that these limited area changes are indicative of changes in the sample as a whole. Additionally, because the surface characteristics of the sample will change as it is loaded, it is difficult to keep the extensometer or strain gauge secured to the sample.

Both strain gages and extensometers measure the stiffness of a material. However, a major problem with both the strain gage and extensometer approach to dynamic material fatigue monitoring is that the strain gages and extensometers cannot be used in a corrosive or extreme temperature environment. This is because the heat or corrosive environments will affect or destroy the equipment in addition to affecting the material under test. This limitation prevents testing for certain application areas. For example, when the space shuttle re-enters the earths atmosphere, temperatures in excess of 3000° F. and a multiplicity of highly reactive ions are encountered. Neither stain gages, nor extensometers could be used under such harsh laboratory conditions.

If extensometers or strain gages cannot be used, monitoring stiffness change using classical methods as a measure of damage is not possible. Therefore, an experimental technique other than life estimation based on the median life or on stiffness degradation should be used for analyzing damage evolution and growth mechanisms throughout life.

SUMMARY OF THE INVENTION

It is therefore an object of the present invention to provide a non-contact method for dynamic fatigue monitoring of polymeric and composite specimens.

It is another object of the present invention to use load and stroke (displacement) signals from an ordinary servo hydraulic test machine to measure quantities such as phase lag and gain to determine damage (% life remaining) and rate of damage in a polymeric or composite specimen.

It is yet another object of the present invention to provide a non-destructive method for determining the residual strength of a polymeric or composite specimen.

According to the invention, a conventional dynamic testing machine is modified to provide for a new method for dynamically monitoring fatigue damage. In operation, a specimen is gripped at two separate locations and cyclically loaded by applying a tension force that elongates or stretches the specimen. As the specimen is cycled and damage occurs, the specimen will become less stiff, i.e. the modulus of elasticity for the material will begin to degrade. As the specimen becomes less stiff, it will take longer for a load which is applied at one end of the specimen to be detected at the other end. In addition, as the specimen fatigues and becomes more elastic, the material will be displaced or stretched a greater distance for a given load.

A cyclic load is applied to a specimen between an upper limit and a lower limit at a predetermined frequency by a conventional dynamic testing machine which has outputs available for measuring load and displacement parameters experienced by the specimen. In the time domain, the graphs of these parameters appear as sine waves having a phase shift relative to one another. This relative phase shift has been found to be related to the rate in which the specimen is being damaged. The gain, or change in the maximum amplitude of the displacement curve over time has been found to be related to the total damage incurred by the specimen.

The phase angle and gain are calculated and plotted for each cycle during the life of the specimen until failure. The phase angle and gain for the specimen are replotted in terms of normalized life. The normalized life is the life of the specimen expressed as a percentage, wherein 0 indicates 100% life remaining and 1 indicates end of life or failure. For example, if the specimen fails at cycle number 100,000, then at cycle number 50,000 the specimen was at 0.5 of its normalized life, i.e. had 50% of life remaining, and at cycle number 100,000 had 0% life remaining. It is observed that phase lag and gain response of specimens, regardless of their respective lives, demonstrate a characteristic behavior. Additionally, the relative change between the initial phase lag and gain values with respect to their final values before specimen fracture, on the average, remains constant. The remaining life and residual strength of similar specimens undergoing cyclic testing, can be accurately determined by observing the gain and phase angle.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
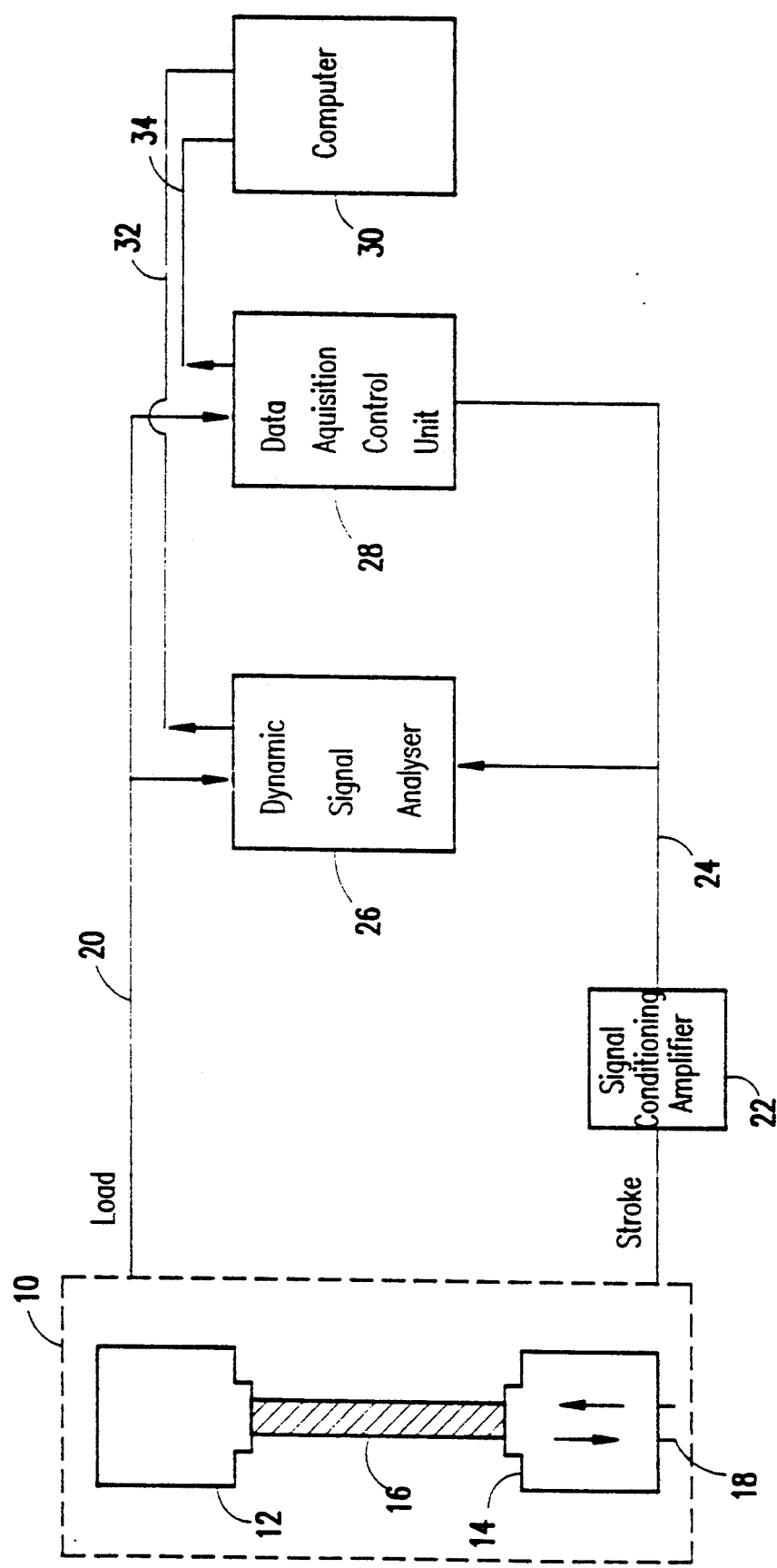
FIG. 1 is a schematic diagram of the dynamic analysis experimental setup.

Referring now to the drawings, and more particularly to FIG. 1, there is shown a servo hydraulic test machine such as an MTS (Material Testing System) 10. An upper gripper 12 and a lower gripper 14 are positioned to hold a specimen 16 in place. The lower gripper 14 is mounted to a piston 18 which moves up and down to alternately apply compression or tension to the specimen 16. The upper gripper 12 remains stationary and a load sensor (not shown) connected thereto provides a load signal 20 indicative of the load which has been transmitted from the lower gripper 14 through the specimen 16 to the upper gripper 12. It is noted that the time it takes for an applied load to propagate between the grippers is dependent upon the elasticity of the specimen 16, i.e. as the specimen 16 becomes more elastic, the load propagation time will tend to increase.

A standard MTS 10 is equipped with a transducer (not shown) which provides a stroke signal 24. Normally this signal 24 is used internally by the MTS 10 to monitor the stroke and to abort a test if the signal indicates that a maximum preset stroke length has been exceeded and there is a danger that a specimen 16 could break. This signal 24 is normally very noisy and weak, which is suitable for its designed purpose; however, to be useful to the present invention, the stroke signal 22 is amplified and filtered by a signal conditioning amplifier 22. Obviously, the transducer could be made more sensitive to accomodate the present application.

Both the load 20 and stroke 24 signals are fed into a dynamic signal (spectrum) analyzer 26 and a data acquisition control unit 28. The load 20 and stroke 24 signals carry thereon signals over a wide spectrum range. The dynamic signal analyzer 26 is set to analyze only the stroke 24 and load 20 signals at the driving frequency of the specimen which is also the frequency at which the MTS 10 cyclically loads the specimen 16. The data acquisition control unit 28 measures voltage parameters of the load 20 and stroke 24 signals. A computer 30 is connected to communicate and correlate with the dynamic signal analyzer 26 and the data acquisition control unit 28, via cables 32 and 34, respectively. The computer 30 calculates and plots a gain and phase angle value for each cycle.

In operation, piston 18 will move down until a maximum preset tension is sensed at upper gripper 12 and then move up until the tension sensed at the upper gripper 12 has decreased to a minimum preset value and the cycle is repeated.

Figure 2:
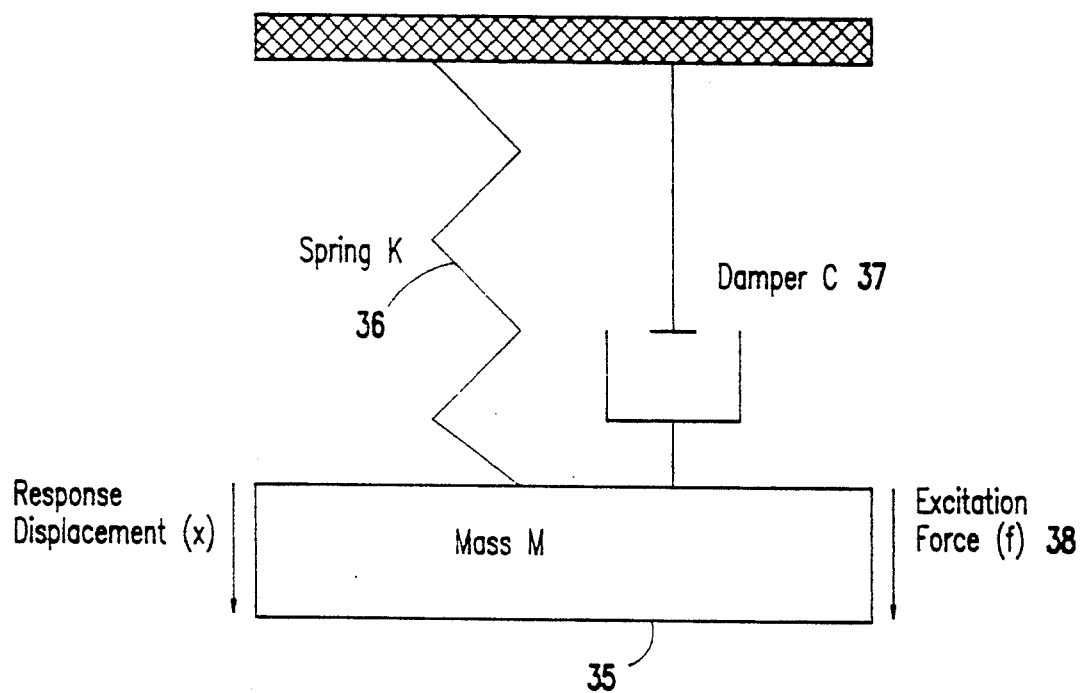
FIG. 2 is a discrete parameter model for a simple mechanical system.

Dynamic analysis of fatigued structures can be easily modeled using a discrete parameter model as illustrated in FIG. 2. The idealized elements are called mass 35, spring 36, damper 37, and excitation force 38. Energy is stored by the system in the mass 35 and the spring 36 in the form of kinetic and potential energy, respectively. Energy enters the system through excitation and is dissipated through damping.

The relationship among the constituents of the system (mass, stiffness, and damping) is given by:

$$m\ddot{x} + c\dot{x} + kx = f(t)$$

The above equation is referred to as the equation of motion for the single degree of freedom (SDOF) system depicted in FIG. 2. The natural frequency and damping factor of the system is calculated using the definitions:

$$\omega_n^2 = \frac{K}{m}, \quad 2\zeta\omega_n = \frac{c}{m} \text{ or } \zeta = \frac{c}{\sqrt{2km}}$$

The natural frequency, $\omega$ is in units of radians per second (rad/s). The typical units displayed on a digital signal analyzer, however, are in Hertz (Hz). The damping factor can also be represented as a percent of critical damping-the damping level at which the system experiences no oscillations. Although there are three damping cases, only the underdamped case ($\zeta < 1$) is generally important for structural dynamics applications.

When there is no excitation, the roots of the equation are shown as:

$$s_{1,2} = -\sigma + j\omega_d$$

Where:
  $\sigma$ is the damping rate, and
  $\omega_d$ is the damped natural frequency.

Each root has two parts: the real part or decay rate, which defines damping in the system and the imaginary part, or oscillatory rate, which defines the damped natural frequency $\omega_d$.

When excitation is applied, such as when a polymeric or composite material specimen is cyclically loaded by an MTS, the equation of motion leads to the frequency response of the system. The frequency response is a complex quantity and contains both real and imaginary parts (rectangular coordinates). It can be presented in polar coordinates as magnitude and phase, as well. Because it is a complex quantity, the frequency response function cannot be fully displayed on a single two dimensional plot. One method of presenting data is to plot the polar coordinates, magnitude and phase versus frequency. At resonance, $\omega = \omega_n$, the magnitude is a maximum and is limited only by the amount of damping in the system. The phase ranges from 0° to 180° and the response lags the input by 90° at resonance.

Using a frequency response of a dynamic signal analyzer, phase lag and compliance between the load and stroke signal can be determined. The frequency response measurement, often called the "transfer function", is the ratio of a system's output to its input, and yields compliance (X/F) as a function of frequency. Frequency response is calculated as the ratio of the cross spectrum to the load signal's power spectrum and is shown as:

$$h(f) = \frac{G_{S1}}{G_{11}}$$

Where:

$G_{S1}$ is the cross spectrum; and
$G_{11}$ is the load signal's power spectrum.

The cross spectrum of the load/stroke signals is calculated by multiplying the complex conjugate of the load spectrum by the stroke spectrum as given by:

$$G_{S1} = (F_S)(F_1^*)$$

Where:

$F_S$ is the stroke signal's linear spectrum; and
$F_1^*$ is the load spectrum's complex conjugate.

The power spectrum measurement shows the load signal in the frequency domain. It is computed by multiplying the FFT of the signal by its complex conjugate.

$$G_{11} = (F_1)(F_1^*)$$

Where:

$F_1$ is the load signal's linear spectrum; and,
$F_1^*$ is its complex conjugate.

It is evident from the above equation that the dynamic compliance of any mechanical structures or systems can be determined using the displacement from any applied forcing function.

Figure 3:
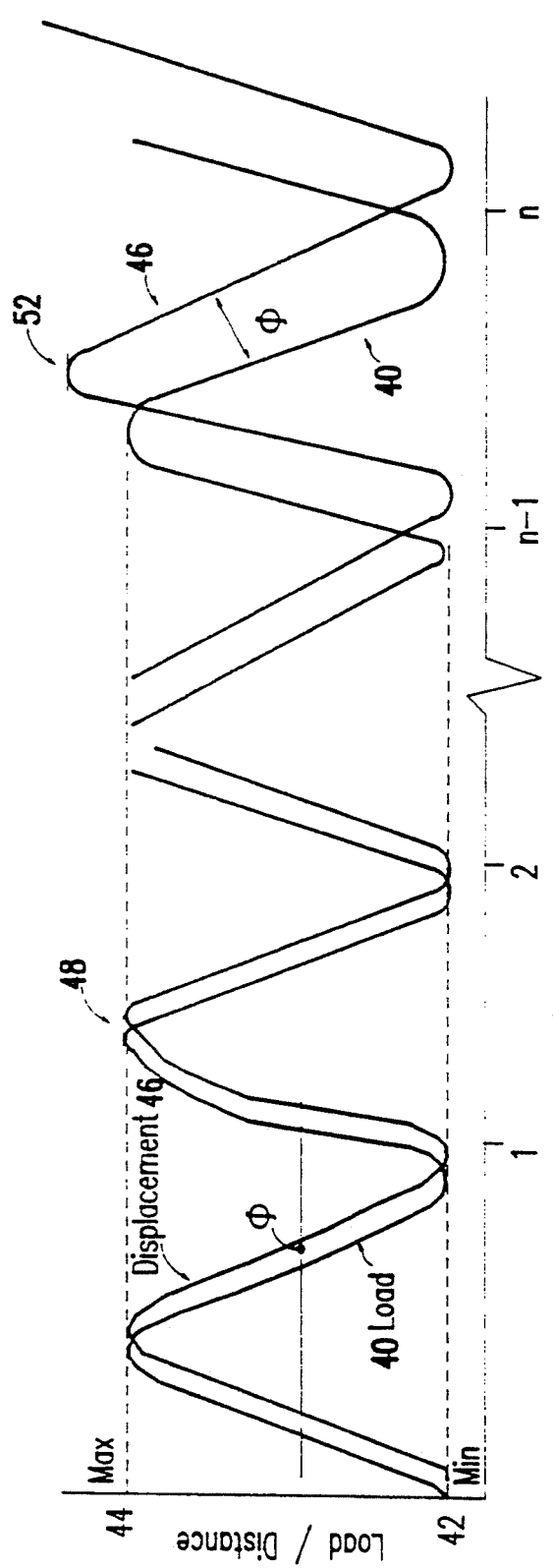
FIG. 3 is a graph showing the load and displacement signals as a function of cycles.

FIG. 3 shows the output of the load and stroke signals plotted against time. Cycle 0 through cycle n are plotted along the abscissa. The amplitude of the load 40 alternates between a minimum tension 42 and a maximum tension 44 from 0 to n cycles. The displacement curve 46 is superimposed onto the load curve 40. It is noted that the load curve 40 leads the displacement curve 46 by an angle $\phi$. We have observed that as the number of cycles increases, the phase angle $\phi$ increases. This is because as the material becomes fatigued and more elastic, the load takes longer to be transmitted through the specimen. Thus, the load curve 40 lags further and further behind the displacement curve 46 as the material approaches failure. Therefore, the relative phase shift between the load curve 40 and the displacement curve 46 is related to the rate of specimen failure.

As the specimen is cyclically loaded and becomes fatigued and more elastic, the amplitude or gain of the displacement curve 46 also increases. After cycle number 1, the amplitude of the displacement curve 46 is at amplitude 48. After n cycles, the amplitude has increased to amplitude 52. The relative difference between amplitude 48 and amplitude 52 is the gain for cycle number n. The gain is observed to be related to the total damage sustained by a specimen.

A detailed study of the damage evolution and life of unidirectional laminates was performed. Specially designed laminates (eight-ply unidirectional panels were made of Hexcel's graphite/epoxy prepreg (AS6/F584)) were fatigued and examined for fiber fracture, remaining strength and life throughout the fatigue life of the specimen.

The specimens 16 were mounted in the MTS 10 as shown in FIG. 1, and the dynamic response measurements recorded with a dynamic data acquisition control unit 28 and an HP 3562A dynamic signal analyzer 26. An HP-9000 computer 30 was used for real time dynamic response monitoring. Phase lag and gain response of the load/stroke signals from the MTS servohydraulic load frame 10 were plotted in conjunction with the load and stroke data. To avoid disk storage overflow, data were sampled according to their relative change with respect to the previous events.

Working in a frequency domain, all the measurements were made at the system's excitation frequency (10K Hz) in a linear resolution mode. First, by using the cross spectrum function, the fundamental frequency was determined. Then the phase lag and gain measurements were made at this frequency using a frequency response measurement function.

Dynamic response for the unidirectional laminate specimens 16 demonstrated a general characteristic behavior. Modeling this behavior made it possible to identify the stage of damage in the material. The gain and phase angle illustrated good correlation with the residual strength, fiber fracture density as well as the remaining life measurements.

Figure 4:
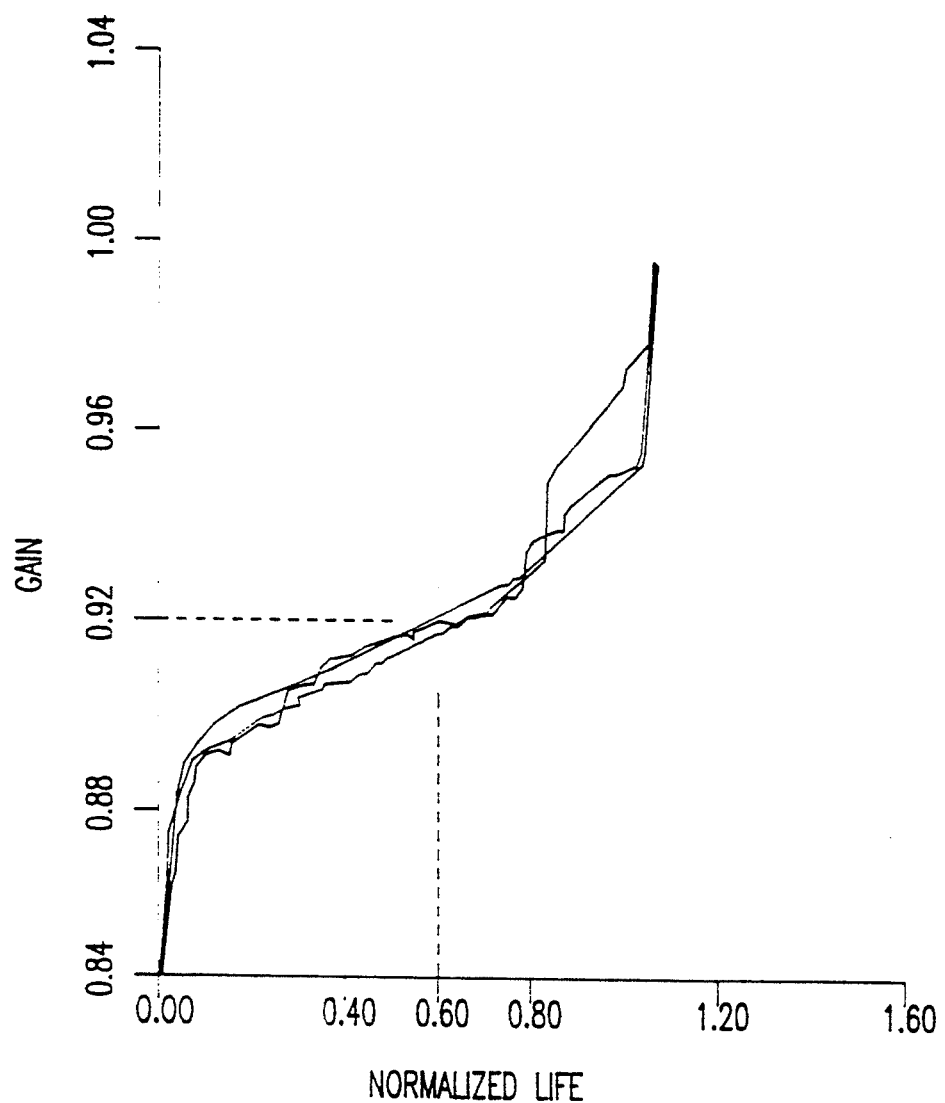
FIG. 4 is a graph showing the gain response over the normalized life of three specimens.

Referring now to FIG. 4 there is shown a normalized life vs. gain response curve for three specimens cyclically loaded at 65% of their ultimate tensile strength until failure. It is noted that all three of the normalized curves indicate that for a given gain, the remaining percent life is approximately the same. Hence, if a fourth specimen is tested and exhibits a gain of 0.92 after 60,000 cycles, then using the previously calculated normalized curves of FIG. 4, it can be accurately predicted that 60% of the specimen's life is past, 40% life remains, and the specimen will fail near 100,000 cycles. Likewise, if a specimen exhibits a gain of 0.92 after only 600 cycles, then it can be accurately predicted that the specimen will fail near 1000 cycles.

Figure 5:
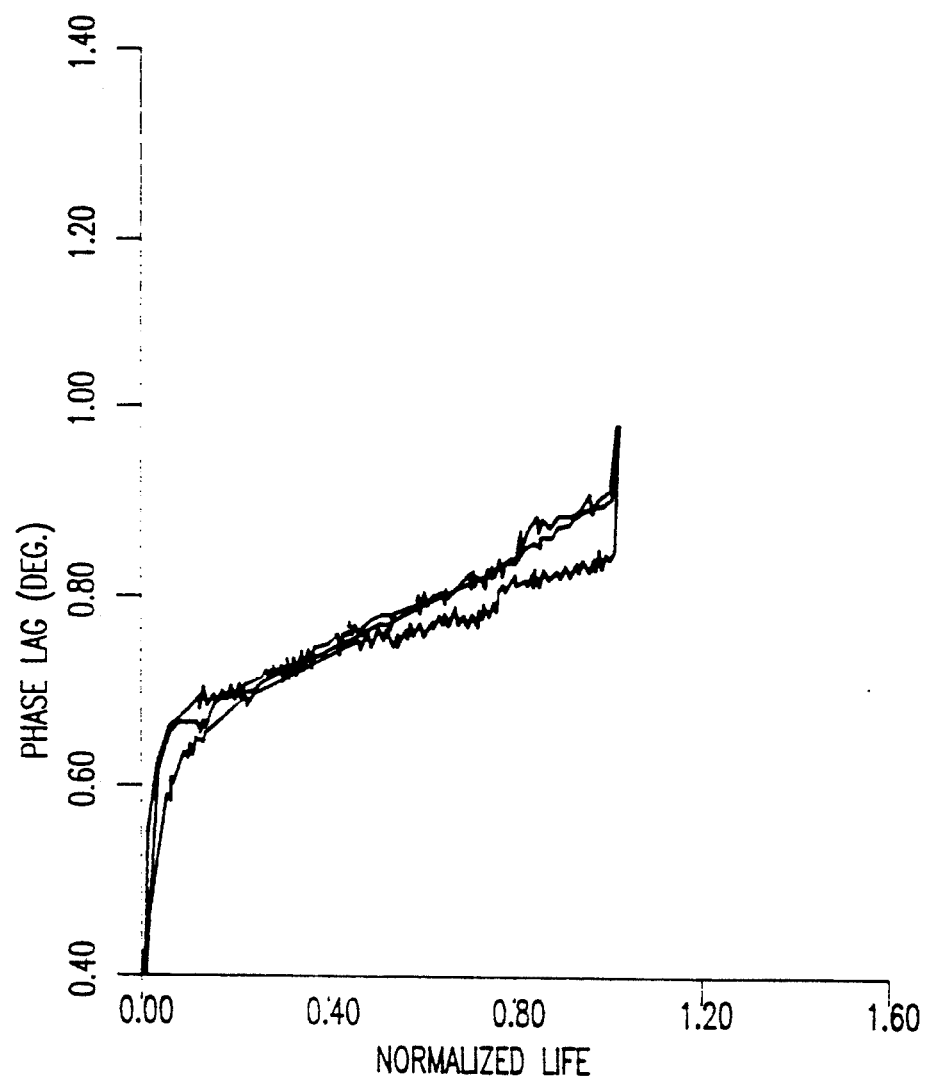
FIG. 5 is a graph showing the phase response over the normalized life of three specimens.

Referring now to FIG. 5, there is shown a normalized life vs. phase angle curve for the same three specimens as those of FIG. 4. The normalized phase lag curve shows a strong correlation with specimen damage. Further, the slope of the curve indicates the rate at which specimen occurs under cyclic loading conditions.

Figure 6:
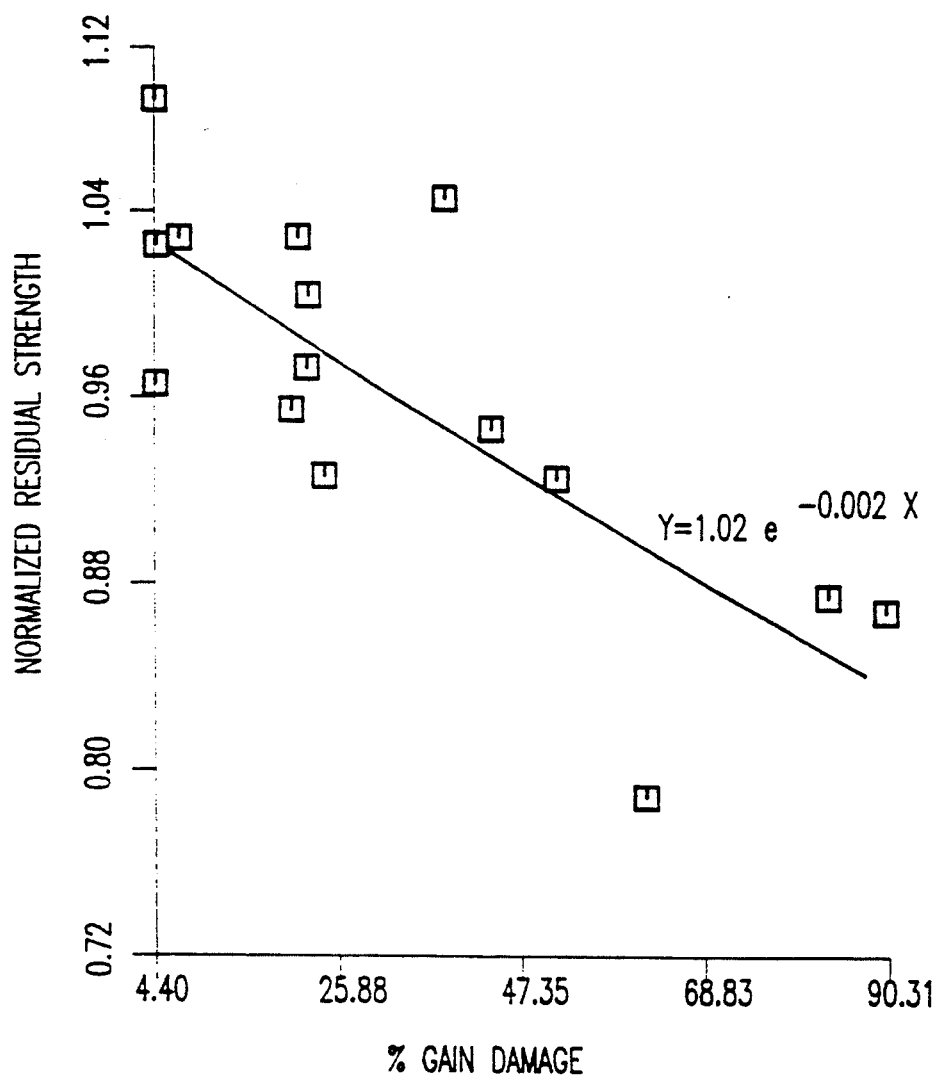
FIG. 6 is a graph showing residual strength degradation as a function of % gain damage.
Figure 7:
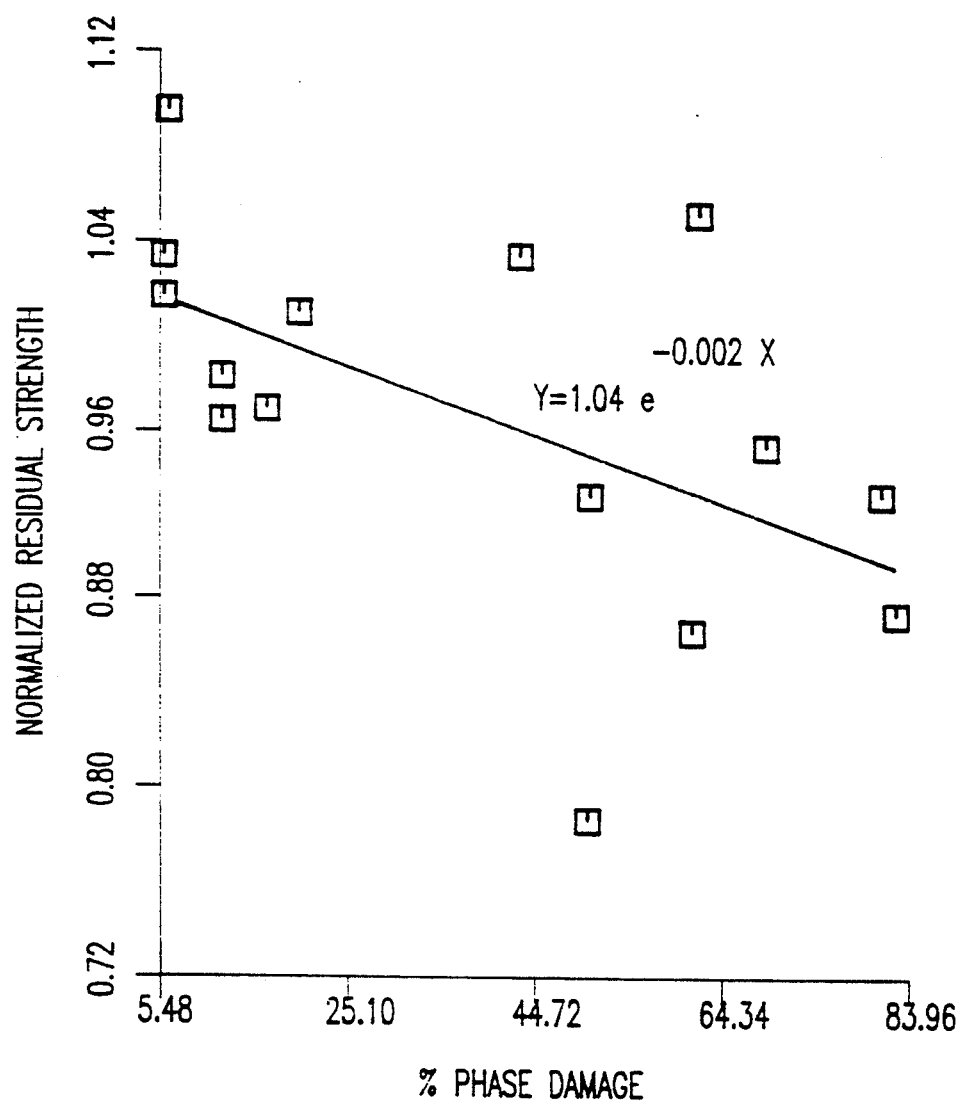
FIG. 7 is a graph showing residual strength degradation as a function of % phase angle damage.

Various specimens were fatigue cycled and stopped based on the percent phase and gain damage. These specimens were later loaded quasi-statically to failure for residual strength measurements. FIG. 6 and FIG. 7 illustrate the residual strength degradation as a function of the percent phase damage and percent gain damage, respectively. It can be seen that the measurements fall into a general, predictable pattern.

Figure 8:
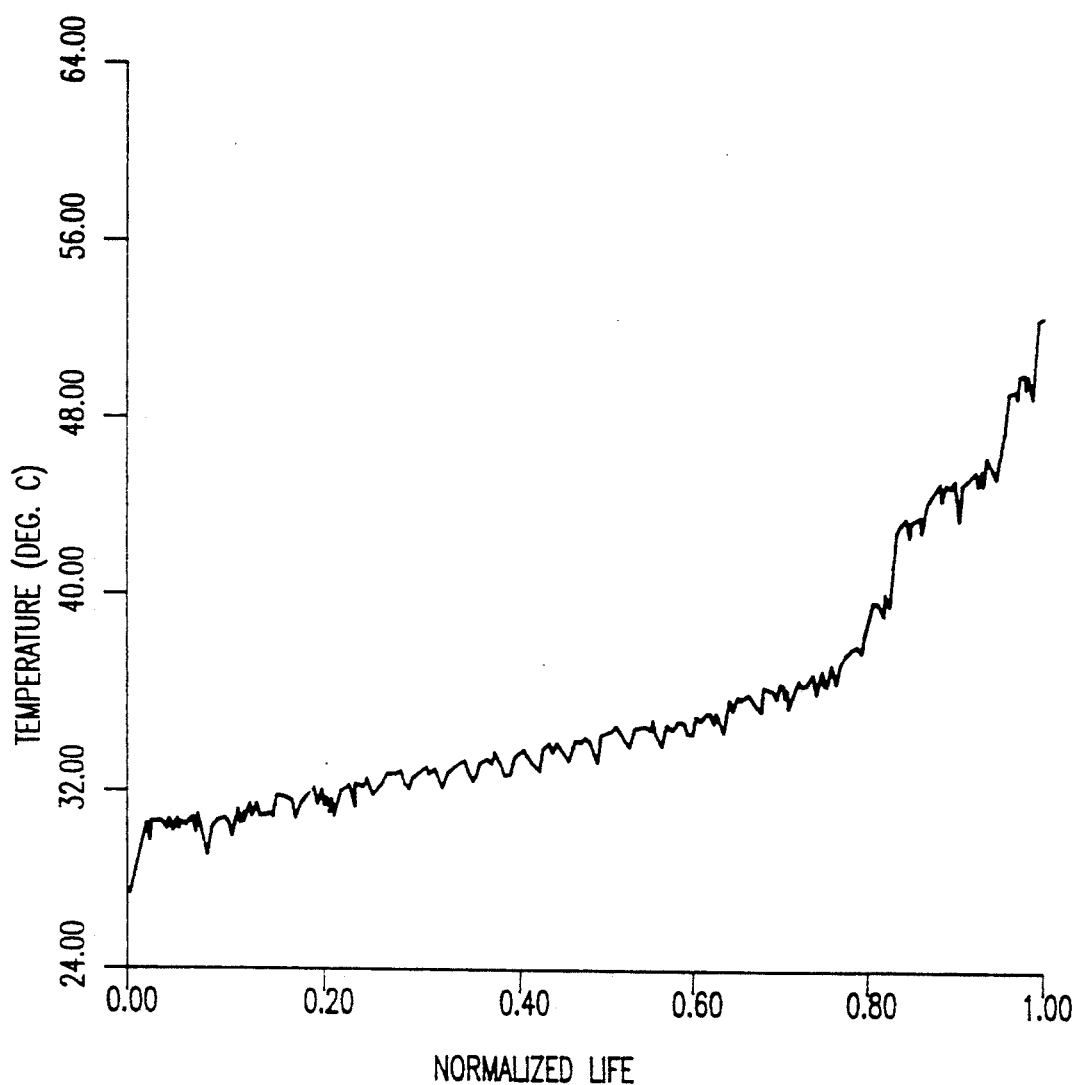
FIG. 8 is a graph showing the temperature response of a specimen.

During the course of the experiments, it was observed that the temperature of the specimen also correlates to specimen damage. FIG. 8 shows the temperature response of a specimen vs. normalized life for a specimen 16 cyclically loaded at 78% of its ultimate tensile strength at a frequency of 10 HZ. The curve indicates that the temperature of a specimen gradually increases from the first few cycles and rapidly increases as the specimen approaches the last quarter of its life.

It is noted that the present invention has many advantages over the prior art. Particularly, the present method requires no surface connections to the specimen under test. This allows for testing in harsh environments. In addition, the present invention provides an accurate way to determine remaining life and residual strength using the load and stroke signals which are readily available on standard testing equipment.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. A method for dynamically monitoring fatigue damage in a specimen, comprising the steps of:
   cyclically applying a load to a specimen, at least a portion of said specimen being displaced from a stationary position by said cyclically applied load;
   detecting said displacement of said portion of said specimen during said step of cyclically applying a load, said step of detecting providing a displacement signal with respect to time;
   sensing a load applied during said step of cyclically applying a load, said step of sensing providing a load signal with respect to time;
   determining a phase difference between said displacement signal and said load signal;
   identifying a change in amplitude of said displacement signal with respect to time; and
   correlating said phase difference and said change in amplitude with specimen damage, whereby increases in phase difference and amplitude of said displacement signal with respect to time corresponds with specimen damage.

2. A method for dynamically monitoring fatigue damage in a specimen as recited in claim 1, wherein said step of correlating provides an indication of residual strength of said specimen.

3. A method for dynamically monitoring fatigue damage in a specimen as recited in claim 1, wherein said step of correlating provides an indication of percent life remaining for said specimen.

4. A method for determining percent life and residual strength remaining in a specimen which is cyclically loaded, comprising the steps of:
   constructing a normalized life v. gain curve for a sample specimen, said curve being characteristic of percent life remaining and residual strength in said specimen;
   cyclically applying a load to a test specimen;
   determining a frequency response of said specimen in terms of displacement gain; and
   comparing displacement gain with said normalized life v. gain curve.

5. A method for determining percent life and residual strength remaining in a specimen which is cyclically loaded, comprising the steps of:
   constructing a normalized life v. phase angle curve for a sample specimen, said curve being characteristic of percent life remaining and residual strength in said specimen;
   cyclically applying a load to a test specimen;
   determining a frequency response of said specimen in terms of a phase angle; and
   comparing said phase angle with said normalized life v. phase angle curve.

6. A method for dynamically monitoring fatigue damage in a specimen, comprising the steps of:
   cyclically applying a load to a specimen, at least a portion of said specimen being displaced from a stationary position by said cyclically applied load;
   detecting said displacement of said portion of said specimen during said step of cyclically applying a load, said step of detecting providing a displacement signal with respect to time;
   identifying a change in amplitude of said displacement signal with respect to time; and
   correlating said change in amplitude with specimen damage.

7. An apparatus for dynamically monitoring fatigue damage in a specimen, comprising:
   means for cyclically applying a load to a specimen which displaces a portion of said specimen from a stationary position;
   means for detecting said displacement of said portion of said specimen and providing a displacement signal with respect to time;
   means for sensing a load and providing a load signal with respect to time;
   means for determining a phase difference between said displacement signal and said load signal;
   means for identifying a change in amplitude of said displacement signal with respect to time; and,
   means for correlating said phase difference and said change in amplitude with specimen damage, whereby increases in phase difference and amplitude of said displacement signal with respect to time corresponds with specimen damage.

8. An apparatus for dynamically monitoring fatigue damage in a specimen as recited in claim 7 wherein said means for correlating provides an indication of residual strength of said specimen.

9. An apparatus for dynamically monitoring fatigue damage in a specimen as recited in claim 7 wherein said means for correlating provides an indication of percent life remaining for said specimen.

10. An apparatus for determining percent life and residual strength remaining in a specimen which is cyclically loaded, comprising:
   means for constructing a normalized life v. gain curve for a sample specimen, said curve being characteristic of percent life remaining and residual strength in said specimen;
   means for cyclically applying a load to a test specimen;
   means for determining a frequency response of said specimen in terms of displacement gain; and means for comparing displacement gain with said normalized life v. gain curve to determine percent life and residual strength remaining in a specimen.

11. An apparatus for determining percent life and residual strength remaining in a specimen which is cyclically loaded, comprising:
   means for constructing a normalized life v. phase angle curve for a sample specimen, said curve being characteristic of percent life remaining and residual strength in said specimen;
   means for cyclically applying a load to a test specimen;
   means for determining a frequency response of said specimen in terms of a phase angle; and
   means for comparing said phase angle with said normalized life v. phase angle curve to determine percent life and residual strength remaining in a specimen.

12. An apparatus for dynamically monitoring fatigue damage in a specimen, comprising:
   means for cyclically applying a load to a specimen which displaces a portion of said specimen from a stationary position;
   means for detecting said displacement of said portion of said specimen and providing a displacement signal with respect to time;
   means for identifying a change in amplitude of said displacement signal with respect to time; and,
   means for correlating said change in amplitude with specimen damage.

13. An apparatus for dynamically monitoring fatigue damage in a specimen as recited in claim 12 wherein said means for cyclically applying a load is a servo hydraulic test machine.

* * * * *